United States Patent [19]

Kamei et al.

[11] Patent Number: 4,833,079
[45] Date of Patent: May 23, 1989

[54] PROCESS FOR PRODUCING 3,7-DIHYDROXYTROPOLONE AND ANTITUMOR USE THEREOF

[75] Inventors: Hideo Kamei; Masaru Ohbayashi; Koji Tomita, all of Tokyo; Koko Sugawara, Wako; Masataka Konishi, Miyamae, all of Japan

[73] Assignee: Bristol-Myers Company, New York, N.Y.

[21] Appl. No.: 927,203

[22] Filed: Nov. 5, 1986

[51] Int. Cl.$^4$ .................... C12P 7/26; C12R 1/465
[52] U.S. Cl. ................................ 435/148; 435/886
[58] Field of Search ............................... 435/148, 886

[56] References Cited

PUBLICATIONS

Chem Abs 109(15) 122100X, Sugawara et al., Jour Antibiot 41(7)862-8 (1988).
Biotech Abs 88-10192, Sugawara et al., Jour Antibiot 41(7)862-8(1988).

Derwent Abs 84-227832/37 (J59134744)8-84.
Derwent Abs 84-227823/37 (J59134720)8-84.
Derwent Abs 790287 B/02 (J53/5954)11-1978.

*Primary Examiner*—Herbert J. Lilling
*Attorney, Agent, or Firm*—David M. Morse

[57] ABSTRACT

The compound 3,7-dihydroxytropolone having the formula

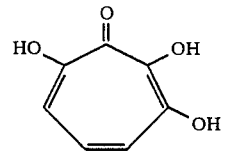

is produced by fermentation of *Streptomyces tropolofaciens* and is found to inhibit the growth of mammalian tumors.

2 Claims, 1 Drawing Sheet

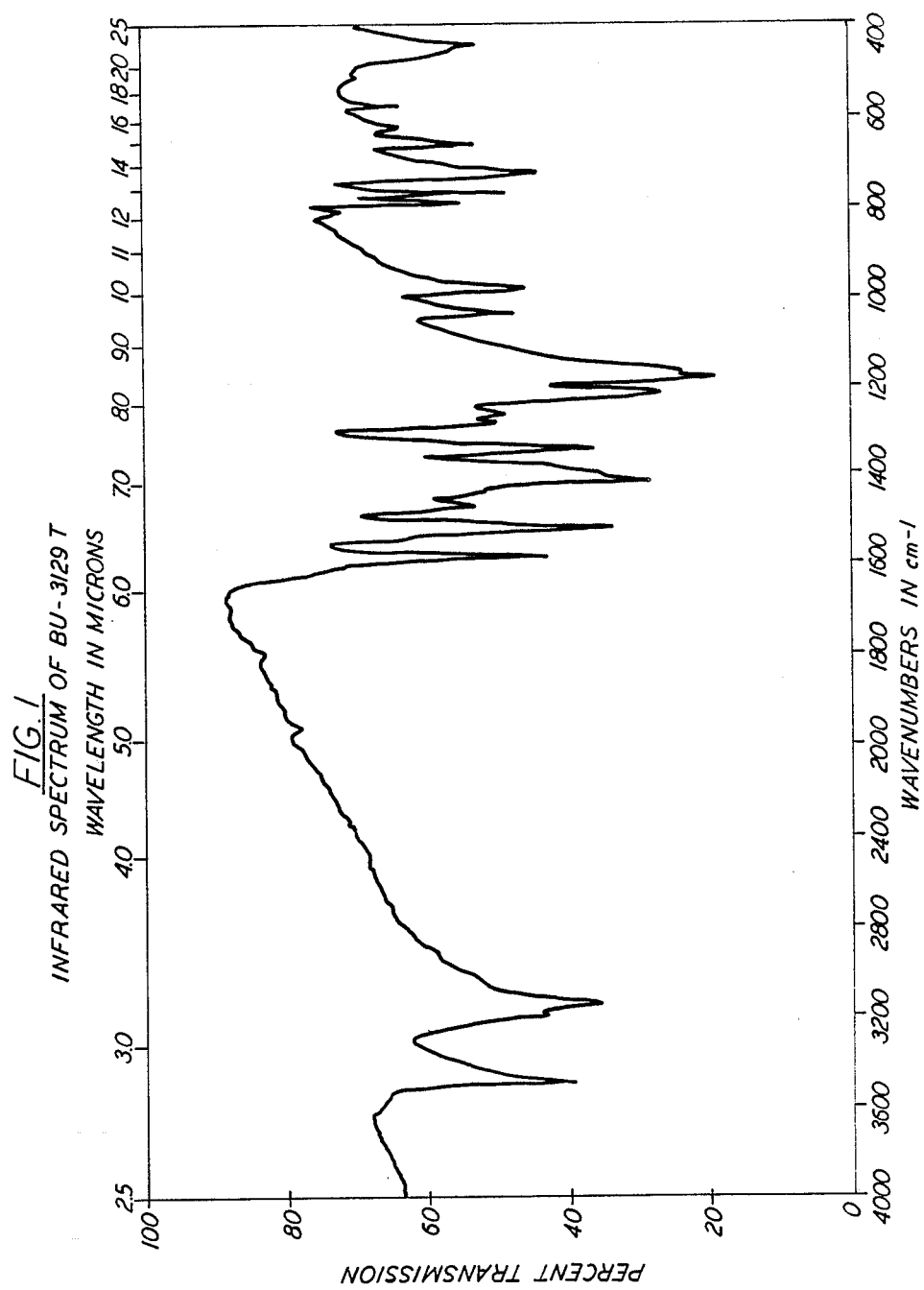

PROCESS FOR PRODUCING 3,7-DIHYDROXYTROPOLONE AND ANTITUMOR USE THEREOF

BACKGROUND OF THE INVENTION

1. Field of the Invention

This invention relates to the preparation by fermentation of a known compound, 3,7-dihydroxytropolone, which has previously been produced only by chemical synthesis.

The invention also relates to the novel discovery that 3,7-dihydroxytropolone inhibits the growth of mammalian tumors and can be used as an antitumor agent for treatment of such tumors.

2. Description of the Prior Art 3,7-Dihydroxytropolone is a known compound which has previously been prepared by chemical synthesis. Nozoe, et. al. in *Bull. Chem. Soc. Japan* 33: 1071, 1960 describe synthesis of 3,7-dihydroxytropolone by heating 3,7-dibromotropolone with sodium β-naphthalenesulfonate in dilute alkaline solution. Kirst, et. al. in *J. Antibiotics* 35 (12): 1651–1657, 1982 disclose synthesis of 3,7-dihydroxytropolone along with 7-hydroxytropolone, 5-hydroxytropolone and 4,7-dihydroxytropolone by persulfate oxidation of tropolone. The Kirst paper indicates that 3,7-dihydroxytropolone possesses antimicrobial activity. Applicants are unaware, however, of any disclosure that 3,7-dihydroxytropolone or its analogs (e.g. 7-hydroxytropolone, 5-hydroxytropolone or 4,7-dihydroxytropolone) possess antitumor activity.

Several natural and synthetic tropolones have been reported in the literature to have antitumor activity. Illustrative of such antitumor tropolone derivatives are those described in Japanese Published Application Nos. 59/134,720, 134,720, 59/134,744, 59/134,745, 54/61,158, 63/25,393, 63/25,367 and Canadian Patent No. 787,451. See also, *J. Med. Chem.* 28(8): 1026–1031, 1985, *J. Med. Chem.* 27(12): 1749–1753, 1984, *Chem. Pharm. Bull.* (Tokyo) 31(8): 2952–1954, 1983, *Boll. Soc. Ital. Biol. Sper.* 43(1): 14–17, 1967, *Nippon Yakurigaku Zasshi* 60: 52–61, 1964, *Nippon Yakurigaku Zasshi* 55: 1061–1064, 1959, *J. Med. Chem.* 24: 251–256, 1981 and *J. Med. Chem.* 26: 1365–1369, 1983.

Japanese Published Application No. 60/228414 discloses tropolone derivatives of the formula

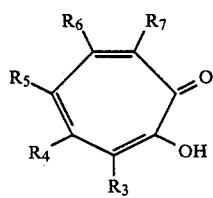

where $R_3$–$R_7$=$H_1$, lower alkyl, OH, $NH_2$, lower alkoxy, halogen, mono- or di-lower alkylamino, COOH or lower alkyloxycarbonyl as being useful for treatment of arteriosclerosis or inflammation. 3,7-Dihydroxytropolone is generically encompassed by the disclosure.

Despite the extensive search for antitumor derivatives of tropolone, there has been no disclosure, as mentioned above, that 3,7-dihydroxytropolone possesses any antitumor activity.

SUMMARY OF THE INVENTION

In one aspect the present invention relates to a new process for preparation of 3,7-dihydroxytropolone which comprises aerobically cultivating a new microorganism designated herein as *Streptomyces tropolofaciens* strain K611-97, ATCC 53548, or a 3,7-dihydroxytropolone-producing mutant thereof, in an aqueous nutrient medium containing assimilable sources of carbon and nitrogen until a substantial amount of 3,7-dihydroxytropolone is produced by said organism in said cultur medium and, optionally, isolating said 3,7-dihydroxytropolone from the culture medium.

In another aspect the invention relates to a pharmaceutical composition for inhibiting the growth of mammalian tumors comprising a tumor-inhibiting amount of 3,7-dihydroxytropolone in admixture with a pharmaceutically acceptable carrier.

In still another aspect the invention relates to a method of inhibiting the growth of mammalian tumors by administering to a mammal bearing such tumor an amount of 3,7-dihydroxytropolone effective to inhibit the growth of the tumor.

DETAILED DESCRIPTION

The novel 3,7-dihydroxytropolone-producing organism, *Streptomyces tropolofaciens* strain K611-97, was isolated from a soil sample collected in Uttar Pradesh State, India, and obtained on an agar medium containing xanthine as a major nitrogen-carbon source. The agar plate was incubated at 47° C. The results of taxonomic studies indicate that strain K611-97 belongs to the genus *Streptomyces* and is proposed as a new species, *Streptomyces tropolofaciens*.

Morphology

Both vegetative and aerial mycelia were formed, which were long, well-branched and not fragmented into short elements. Chains of arthrospores were born on the aerial hyphae. The spore-chain morphology was as follows:

(1) Straight or hook and short chains containing 5 to 10 spores per chain, mainly on natural organic media.

(2) Chains of open or compact spirals, containing 10 to 50 spores per chain in chemically defined media such as ISP medium No. 4.

(3) Sporophores with monopodial or pseudoverticillate branching.

The spores were spherical to oblong in shape (0.5 to 0.7 by 0.6 to 1.2 μm) and had hairy surface. Large number of long hairs were formed in the spores of compact spirals (subgroup $A^7$), while no hairs or fewer and shorter hairs than the subgroup A were seen in the spores of straight or open-spiral chains (subgroup C and B). Sporangium, motile spore and sclerotium were not observed.

Cultural and Physiological Characteristics

Strain K611-97 grew well and sporulated both in nutritionally rich media and chemically defined media including Czapek's sucrose-nitrate agar. The aerial mass color was Gray series. A red pigment in the substrate mycelia was formed in Czapek's agar, ISP media Nos. 2, 4 and 7. An orange yellow pigment in the substrate mycelium was also observed mainly in organic media. Both pigments were not pH-indicator. Melanin and other diffusible pigment were not formed. Tyrosinase activity was negative. It tolerated NaCl at 6% or less, but not at 8%. The temperature range for growth was 15 to 49° C., and no growth was observed at 52° C. Along the diagnostic sugars, which were described in the characterization of species of the genus Streptomyces[1], all of the sugars were utilized for growth except for raffinose.

Cell Chemistry

The whole cell hydrolyzate contained LL-diaminopimelic acid and none of diagnostic sugars.

Determination of Taxonomic Position

The above-mentioned characteristics indicated that strain K611-97 belongs to the genus Streptomyces. According to the description of the genus Streptomyces by Pridham and Tresner[1], the major characteristics of strain K611-97 are summarized as follows:

(1) Aerial mycelium, gray (GY).
(2) Spore chain morphology, Spirales (S).
(3) Melanoid pigments, none (C-).
(4) Spore wall ornamentation, hairy (H).

Comparisons of strain K611-97 to eleven known species of this species group are shown in Table 3. A red pigment in the vegetative mycelium which is seen in strain K611-97, is not produced by any of the eleven known species. In addition, strain K611-97 is differentiated from these known species in the carbohydrate utilization profile, the maximum growth temperature and/or other cultural and physiological characteristics. Based on the comparative studies of strain K611-97 to the relevant species, the strain is proposed as a new species, *Streptomyces tropolofaciens*. The type strain is K611-97 which is a single isolate. This isolate has been deposited with the American Type Culture Collection (Rockville, Md., U.S.A.) and given the accession number ATCC 53548.

It is to be understood that for the production of 3,7-dihydroxytropolone according to the present invention, limitation to the specific strain described above is not intended. It is especially desired and intended to include within the scope of this invention other 3,7-dihydroxytropolone-producing strains of *Streptomyces tropolofaciens* having the characteristics of ATCC 53548 or mutants thereof produced by known procedures such as irradiation with X-rays or ultraviolet light, treatment with nitrogen mustards, phage exposure, and the like.

References (1) Pridham, T. G. and H. D. Tresner : Genus Streptomyces Waksman and Henrici, 1943, P. 748–829. In R. E. Buchanan and N. E. Gibbons (ed.), Bergey's Manual of Determinative Bacteriology, 8th ed. 1974. The Williams and Wilkins Co., Baltimore.

(2) Mertz, F. P. and C. E. Higgens: Streptomyces capillispiralis sp. nov. Intl. J. Syst. Bacterial. 32: 116–124, 1982.

(3) Shirling, E. B. and D. Gottlieb: Cooperative description of type cultures of Streptomyces. III. Additional species descriptions from first and second studies. Intl. J. Syst. Bacteriol. 18 : 279–392, 1968.

(4) Liu, W.; D. S. Slusarchyk, G. Astle, W. H. Trejo, W. E. Brown and E. Meyers: Ionomycin, a new polyether antibiotic. J. Antibiotics 31: 815–819, 1978.

(5) Komatsu, N.; K. Kimura, S. Abe and Y. Kagitani: *Streptomyces spadicogriseus* a new species producing anthramycin. J. Antibiotics 33: 54–60, 1980.

(6) Namiki, S.; K. Kangouri, T. Nagate, H. Hara, K. Sugita and S. Omura: Studies on the α-glucoside hydrolase inhibitor, adiposin. II. Taxonomic studies on the producing microorganism. J. Antibiotics 35: 1156–1159, 1982.

(7) Dietz, A. and J. Mathews : Characterization of hairy-spored streptomycetes. II. Twelve additional cultures. Intl. J. Syst. Bacteriol. 27: 282–287, 1977.

TABLE 1

Cultural Characteristics of Strain No. K611-97*[1]

| | |
|---|---|
| Sucrose-nitrate agar (Czapek-Dox agar) | G: Abundant<br>R: Light grayish red (18)*[2]<br>A: Abundant; light gray (264)<br>D: Pale yellowish pink (31) |
| Tryptone-yeast extract broth (ISP No. 1) | G: Abundant; floccose and not turbid<br>D: None |
| Yeast extract-malt extract agar (ISP No. 2) | G: Abundant<br>R: Grayish reddish orange (39)<br>A: Abundant; pinkish gray (10)<br>D: None |
| Oat meal agar (ISP No. 3) | G: Moderate<br>R: Colorless<br>A: Moderate; light gray (264)<br>D: None |
| Inorganic salts-starch agar (ISP No. 4) | G: Abundant<br>R: Light reddish brown (42)<br>A: Abundant; medium gray (265)<br>D: None |
| Glycerol-asparagine agar (ISP No. 5) | G: Abundant<br>R: Colorless or strong orange (50)<br>A: Abundant medium gray (265)<br>D: None |
| Peptone-yeast extract-iron agar (ISP No. 6) | G: Abundant<br>R: Strong orange yellow (68)<br>A: Poor; white (263)<br>D: Strong yellow (84) |
| Tyrosine agar (ISP No. 7) | G: Abundant<br>R: Dark red (16)<br>A: Abundant; light gray (264)<br>D: None |
| Glucose-asparagine agar | G: Abundant<br>R: Brilliant orange yellow (67)<br>A: Abundant; white (263)<br>D: None |
| Nutrient agar | G: Moderate<br>R: Brilliant orange yellow (67)<br>A: Poor; white (263)<br>D: Medium yellow (87) |
| Bennett's agar | G: Abundant<br>R: Brilliant orange yellow (67)<br>A: Moderate; light gray (264)<br>D: None |

*[1]Observation after incubation at 28° C. for 2 to 3 weeks
*[2]Color and number follow ISCC-NBC designation

TABLE 2

Physiological Characteristics of Strain K611-97

| Hydrolysis of: | | | |
|---|---|---|---|
| | | D-Xylose | + |
| | | D-Ribose | + |
| Gelatin | − | L-Rhamnose | + |
| Starch | + | D-Glucose | + |
| Milk peptonization | + | D-Galactose | + |
| Milk coagulation | − | D-Fructose | + |
| | | D-Mannose | + |
| Production of: | | L-Sorbose | − |
| | | Sucrose | + |
| Nitrate reductase* | +,− | Lactose | + |
| Tyrosinase | − | Cellobiose | + |
| | | Melibiose | + |
| Tolerance to: | | Trehalose | + |
| | | Raffinose | − |
| 0.01% (w/v) lysozyme | +(w)*** | D-Melezitose | − |

TABLE 2-continued

| Physiological Characteristics of Strain K611-97 | | | |
|---|---|---|---|
| 6% (w/v) NaCl | +(w) | Soluble starch | + |
| 8% (w/v) NaCl | − | Celluose | − |
| | | Dulcitol | − |
| Growth at: | | Inositol | + |
| | | D-Mannitol | + |
| pH 5.5 to 12.0 | + | D-Sorbitol | − |
| 15° C. to 49° C. | + | Salicin | + |
| 13° C. and 52° C. | − | Keratin | − |
| Utilization of**: | | | |
| Glycerol | + | | |
| D-Arabinose | +(w) | | |
| L-Arabinose | + | | |

*Positive in Czapek's sucrose-nitrate broth, and negative in peptone-nitrate broth
**Basal medium: Pridham-Gottlieb medium (ISP No. 9)
***(w): weak

TABLE 3

Differential Characteristics of Strain K611-97 and Eleven Relevant Streptomyces Species, Which Have Gray Aerial Mycelium, Spiral Spore Chain, Hairy Spore and Negative Melanin

| Organism | Distinct color of vegetative mycelium | Utilization of | | | | | Growth at 47.5° C. | Additional differences |
|---|---|---|---|---|---|---|---|---|
| | | Xyl | Rham | Suc | Raf | Inos | | |
| Strain K611-97 | Red and orange yellow | + | + | + | − | + | + | |
| S. culvus ATCC 13382[2] | Brownish black | + | + | + | + | + | + | No aerial mycelium in ISP medium No. 5 and Czapek's agar. Negative starch hydrolysis. |
| S. cyanoalbus ATCC 23902[1],[3] | Blue or green | + | + | + | + | − | | Greenish aerial mycelium on ISP medium nos. 2 and 4. |
| S. finlayi ATCC 23906[1],[3] | Green to yellowish green | + | + | ± | − | − | | — |
| S. flaveolus ATCC 3319[1],[2] | None | + | + | + | + | + | − | No or trace aerial mycelium in ISP medium nos. 2 and 5, Bennett's agar and Czapek's agar. Negative starch hydrolysis. |
| S. herbiforis INHI 10[1] | Grass-green | + | + | + | + | − | | — |
| S. pactum NRRL 2939[1] | None | − | − | − | − | − | | Poor growth on Czapek's agar. |
| S. conglobactus ATCC 31005[4] | Light green | + | − | − | + | − | | A salt and pepper appearance on surface of ISP medium No. 2, because of areas of dense and no sporulation. |
| S. heimi ATCC 25460[2] | None | + | + | + | − | + | | Fair growth in ISP medium nos. 2 and 4. Whitish pink aerial mycelium on Bennett's agar. Negative starch hydrolysis. |
| S. spadicogriseus ATCC 31179[5] | None | + | − | − | − | − | − | Poor growth on Czepak's agar. Gelatin liquefaction. |
| S. capillispiralis NRRL 12279[2] | Dark Brown | + | + | − | − | + | − | Reddish gray aerial mycelium on ISP medium No. 2. No aerial mycelium on Bennett's agar. Negative starch hydrolysis. |
| S. calvus TM-521[6] | None | + | − | ± | ± | − | − | White, scant aerial mycelium on Czapek's agar. Gelatin liquefaction. | nutrient medium should also contain an assimilable nitrogen source such as fish meal, soybean meal, peptones, ammonium salts, yeast extract, etc. Nutrient inorganic salts may also be advantageously incorporated in the culture medium, and such salts may comprise any of the usual salts capable of providing sodium, potassium, ammonium, calcium, phosphate, sulfate, chloride, bromide, nitrate, carbonate or like ions.

Production of 3,7-dihydroxytropolone can be effected at any temperature conducive to satisfactory growth of the organism, e.g. 15° C. to 49° C., and is conveniently carried out at a temperature of about 28° C. Ordinarily, optimum production in tanks is reached in about 4–5 days.

Submerged aerobic culture conditions are the conditions of choice for the production of 3,7-dihydroxy-

DESCRIPTION OF THE DRAWINGS

FIG. 1 shows the infrared absorption spectrum of BU-3129T (3,7-dihydroxytropolone) (KBr).

PRODUCTION OF 3,7-DIHYDROXYTROPOLONE 3,7-Dihydroxytropolone may be prepared according to the present invention by cultivating a 3,7-dihydroxytropolone-producing strain of Streptomyces tropolofaciens having the dentifying characteristics of ATCC 53548, or a 3,7-dihydroxytropolone-producing mutant thereof, under submerged aerobic conditions in an aqueous nutrient medium. The organism is grown in a nutrient medium containing an assimilable carbon source, for example an assimilable carbohydrate. Examples of suitable carbon sources include xylose, ribose, rhamnose, glucose, galactose, fructose, mannose, sucrose, lactose, soluble starch, inositol, mannitol and trehalose. The tropolone. For preparation of relatively small amounts, shake flasks and surface culture can be employed, but for the preparation of larger amounts, submerged aerobic culture in sterile tanks is preferred. The medium in the sterile tank can be inoculated with a sporulated suspension, but because of the growth lag experienced when a sporulated suspension is used as the inoculum, the vegetative form of the culture is preferred. Accordingly, it is desirable first to produce a vegetative inoculum of the organism by inoculating a relatively small quantity of culture medium with the spore form of the organism and, when a young active vegetative inoculum has been obtained, to transfer the vegetative inoculum aseptically to a large tank. The fermentation medium in which the vegetative inoculum is produced can be either the same as or different from the medium used for the large scale production.

The concentration of 3,7-dihydroxytropolone in the fermentation medium can readily be followed during the course of the fermentation by testing samples of the culture for their inhibitory activity against *Cryptococcus neoformans* IAM 4514 using the paper disc-agar plate assay technique.

After optimum broth potency has been obtained the 3,7-dihydroxytropolone in the broth is separated from the mycelia and undissolved solids by conventional means such as filtration or centrifugation. The supernate is then subjected to conventional chromatographic purification techniques to obtain 3,7-dihydroxytropolone in purified form. Example 2 below illustrates one such isolation and purification procedure.

The purified material obtained by the above procedure was first designated as compound BU-3129T and the physicochemical characteristics of BU-3129T were examined to determine the structure of the compound. The characterizing properties are indicated below.

BU-3129T was readily soluble in dimethylformamide and dimethylsulfoxide, slightly soluble in water, methanol and ethanol but practically insoluble in other organic solvents. It showed positive response to ferric chloride and negative response to ninhydrin, anthrone and Fehling reaction. BU-3129T crystals did not show a definite melting point and gradually sublimed over 166° C. The molecular formula of $C_7H_6O_4$ was assigned for BU-3129T based on its high resolution mass spectral results (M+m/z 154.0265) and microanalysis. The antibiotic exhibited strong absorption at 273, 340 (shoulder), 351 and 359 nm in ethanol, at 265, 329 and 366 nm in acidic ethanol and at 224, 283, 340 and 354 nm in alkaline ethanol. The physico-chemical data of BU-3129T are summarized in Table 4. The IR spectrum of BU-3129T in KBr pellet is shown in FIG. 1.

TABLE 4

| Physico-chemical Properties of BU-3129T | |
|---|---|
| Nature: | Pale yellow neeldes |
| M.p.: | sublimes at >166° C. |
| UV $\gamma_{max}$ nm ($\epsilon$) | |
| in EtOH: | 273(46,816), 340$^{sh}$(6,083), 351(6,853) 359(6,699) |
| in 0.01 N HCl—EtOH: | 265(55,902), 329(5,313), 366(3,542) |
| in 0.01 N NaOH—EtOH: | 224(7,161), 283(41,657), 340(7,084), 354(7,007) |
| Microanalysis: | Calcd for $C_7H_6O_4$   Found |
|  | C 54.55             C 53.99 |
|  | H 3.92              H 3.68 |
| Mass spectrum (High resolution electron impact mass spectrum): | |
| observed m/z | 154.0264 (M+, $C_7H_6O_4$ calcd 154.0266) 126.0317 (M+—CO, $C_6H_6O_3$ calcd 126.0317) 108.0211 (M+—$H_2O$—Co, $C_6H_4O_2$ calcd 108.0211) 80.0262 (M+2CO—$H_2O$, $C_5H_4O$ calcd 80.0262) |
| $^1$H-NMR, $\delta$ in ppm, im DMSO-$d_6$: | 7.02 (broad singlet) |
| $^{13}$C-NMR, $\delta$ in ppm, in DMSO-$d_6$: | 117.5, 127.1, 156.5, 156.7 |

STRUCTURAL STUDIES

BU-3129T was given the molecular formula of $C_7H_6O_4$ by the mass spectrum and microanalysis. The high resolution mass spectrum produced strong fragment ions caused by expulsion of CO and/or $H_2O$ from the molecular ion : m/z 126.0317 (M$^{30}$-CO), m/z 108.0211 (M+-$H_2O$-CO) and m/z 80.0262 (M$^{30}$—2CO-$H_2O$) The IR spectrum of BU-3129T exhibited strong absorption at 3490, 1590, 1520, 1410, 1210 and 1180 cm$^{-1}$. Its $^1$H—NMR showed only one signal at $\delta$ : 7.02 (broadsinglet) and $^{13}$C—NMR four carbon peaks at $\delta$ :

117.5, 127.1, 156.5 and 156.7 ppm indicating a tautomeric structure. These data combined with the characteristic UV spectrum suggested 3,7-dihydroxytropolone for BU-3129T. In order to confirm the proposed structure, 3,7-dihydroxytropolone was synthesized by the persulfate oxidation of tropolone. 3,7-Dihydroxytropolone was separated from coproduced 5-hydroxy, 7-hydroxy and 4,7-dihydroxy analogs by counter current distribution (chloroform-toluene-methanol-water=15:15:23:7) and purified by Sephadex LH-20 chromatography. BU-3129T was identical in all respects with chemically synthesized 3,7-dihydroxytropolone.

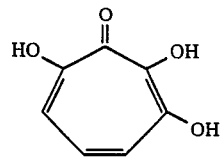

BU-3129T

BIOLOGICAL ACTIVITY

BU-3129T (3,7-dihydroxytropolone) and its analogs were tested for in vitro cytotoxicity against logarithmically growing murine melanoma tumor cells in liquid culture. B16-F10 cells ($4 \times 10^4$ cells) in the enriched MEM (Minimum essential medium (Eagle's)) containing test material solution were planted into wells of 96-well microtiter plates and incubated at 37° C., with 5% $CO_2$ under high humidity for 72 hours. After staining with neutral red, cytotoxicity of test material was determined colorimetrically. The inhibitory effects on macromolecule biosynthesis were examined in cultured L1210 leukemia cells. L1210 cells ($5 \times 10^5$ cells) were exposed to radioactive precursors ($^3$H-thymidine, $^{14}$C-uridine and $^3$H-leucine) for 60 min after the treatment with test material for 15 min. The incorporated radioactivities into acid-insoluble fractions were measured by using a liquid scintillation counter. The in vivo antitumor activity of BU-3129T was determined in male BDF$_1$ mice against leukemia P388 and melanoma B16. Leukemia P388 and melanoma B16 were inoculated by the intraperitoneal injection at $10^6$ cells and 0.5 ml of a 10% tumor brei per mouse, respectively. Test material was administered to mice intraperitoneally once daily through 1 to 9 days after tumor implantation. Tropolone and mitomycin C were comparatively tested in the experiments.

BU-3129T (3,7-dihydroxytropolone) was the most potent in the in vitro cytotoxicity test follow by 7-hydroxytropolone, 4,7-dihydroxytropolone, tropolone and 5-hydroxytropolone. BU-tropolone. BU-3129T showed non-specific inhibitory effects on DNA, RNA and protein biosynthesis with the IC50 values of 9 to 14 mcg/ml. When BU-3129T was administered to mice bearing murine tumors, it exhibited significant antitumor activity against melanoma B16, while no activity was demonstrated against leukemia P388. Tropolone did not show any activity against melanoma B16 at the doses tested.

TABLE 5

In Vitro Cytotoxicity and Inhibition of Macromolecule Biosynthesis

| Compound | Cytotoxicity vs B16 IC50 (mcg/ml) | Inhibition of macromolecule biosynthesis vs L1210 IC50 (mcg/ml) | | |
|---|---|---|---|---|
| | | DNA | RNA | Protein |
| BU-3129T (3,7-dihydroxytropolone) | 0.04 | 9.4 | 14 | 11 |
| 4,7-dihydroxytropolone | 0.38 | 39 | >100 | >100 |
| 7-hydroxytropolone | 0.30 | 21 | 41 | >100 |
| 5-hydroxytropolone | 2.4 | >100 | >100 | 100 |
| Tropolone | 1.8 | 2.2 | 20 | 9.9 |
| Mitomycin C | 2.0 | not done | | |

TABLE 6

Antitumor Activity against Leukemia P388 and Melanoma B16 in Mice

| Compound | Dose qd 1→9, ip (mg/kg/day) | MST (days) | T/C (%) | Average weight change on day 5 (g) |
|---|---|---|---|---|
| vs Leukemia P388 | | | | |
| BU-3129T | 2.5 | 10.0 | 95 | −0.2 |
| | 1.3 | 11.0 | 105 | +0.4 |
| | 0.63 | 10.0 | 95 | +0.4 |
| | 0.31 | 11.0 | 105 | +1.2 |
| | 0.16 | 11.0 | 105 | +0.0 |
| Mitomycin C | 1.3 | 21.0 | 200 | +0.2 |
| | 0.63 | 21.0 | 200 | +0.2 |
| | 0.31 | 16.0 | 152 | +0.8 |
| | 0.16 | 15.0 | 143 | +0.8 |
| | 0.08 | 12.0 | 114 | +1.2 |
| Vehicle | — | 10.5 | — | +0.7 |
| vs Melanoma B16-Exp. 1 | | | | |
| BU-3129T | 5.0 | tox | — | — |
| | 2.5 | 12.0 | 75 | −0.8 |
| | 1.3 | 29.0 | 181 | +0.4 |
| | 0.63 | 23.0 | 144 | +1.0 |
| | 0.31 | 18.0 | 113 | +1.2 |
| | 0.16 | 16.0 | 100 | +0.4 |
| Mitomycin C | 1.0 | 27.0 | 169 | +0.6 |
| | 0.3 | 22.0 | 138 | +0.4 |
| | 0.1 | 16.0 | 100 | +1.0 |
| Vehicle | — | 16.0 | — | +1.3 |
| vs Melanoma B16-Exp. 2 | | | | |
| Tropolone | 30 | 18.0 | 106 | +2.0 |
| | 10 | 18.0 | 106 | +3.3 |
| | 3.0 | 17.5 | 103 | +2.5 |
| | 1.0 | 19.0 | 112 | +2.3 |
| Vehicle | — | 17.0 | — | +1.9 |

The data presented above indicates that 3,7-dihydroxytropolone is 10 to 40 times more cytotoxic against B16 melanoma than tropolone and the hydroxytropolones compared. This activity makes 3,7-dihydroxytropolone distinct among the tropolone compounds so far reported.

The data described above demonstrates that 3,7-dihydroxytropolone possesses marked inhibitory action against mammalian malignant tumors.

According to one aspect of the invention, therefore, there is provided a method for therapeutically treating a mammalian host affected by malignant tumor cells sensitive to 3,7-dihydroxytropolone which comprises administering to said host an effective tumor-inhibiting dose of 3,7-dihydroxytropolone.

In another aspect a pharmaceutical composition is provided which comprises an effective tumor-inhibiting amount of 3,7-dihydroxytropolone in combination with an inert pharmaceutically acceptable carrier or diluent. These compositions may be made up in any pharmaceutical form appropriate for parenteral, enteral or topical administration.

Suitable pharmaceutically acceptable carriers include, but are not limited to, water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidone, etc.

The pharmaceutical preparations can be sterilized and, if desired, mixed with auxiliary agents, e.g. lubricants, preservatives, stabilizers, wetting agents, emulsifiers, salts for influencing osmotic pressure, buffers, coloring, flavoring and/or aromatic substances1 which do not deleteriously interact with the active compound.

For parenteral administration, solutions are particularly suitable, including oily and aqueous solutions, but formutations can also be in the form of suspensions, emulsions, implants or suppositories. Ampoules are convenient unit dosages.

It will be understood that preferred dosages of 3,7-dihydroxytropolone used will vary according to the particular composition formulated, the mode of application and the particular situs, host and disease being treated. Many factors that modify the action of the drug will be taken into account by those skilled in the art, e.g. age, body weight, sex, diet, time of administration, route of administration, rate of excretion, condition of the host, drug combinations, reaction sensitivities and severity of the disease. Optimal dosages for a given set of conditions can be ascertained by those skilled in the art using conventional dosage determination tests.

Without further elaboration it is believed that one skilled in the art can, using the preceding description, utilize the present invention to its fullest extent. The following preferred specific embodiments are therefore to be construed as merely illustrative and not limiting.

EXAMPLE 1

Fermentation of 3,7-Dihydroxytropolone (BU-3129T)

A loopful of *Streptomyces tropolofaciens* No. K611-97, taken from a mature slant culture was inoculated into 500-ml Erlenmeyer flask containing 100 ml of a seed medium consisted of 3% soybean meal, 2% corn starch, 0.33% $MgSO_4.7H_2O$ and 1% $CaCO_3$, the pH being adjusted to 7.0 before sterilization. The flask was then incubated at 28° C. for 4 days on a rotary shaker (200 rpm) and 5 ml of the growth was transferred into 500-ml Erlenmeyer flask containing 100 ml of a fermentation medium having the same composition as the seed medium. The fermentation was carried out at 28° C. for 6 days on a rotary shaker. The antibiotic production was monitored by the paper-disc agar diffusion method against *Cryptococcus neoformans* IAM 4514 as a test organism. For a large scale production, the fermentation studies were carried out in stainless-steel fermentors. The culture was prepared in twenty 500-ml Erlenmeyer flasks incubated at 32° C. for 4 days on the rotary shaker. The resultant culture was transferred into a 200-liter tank fermentor containing 120 liters of a production medium. The seed and production media consisted of 3% soybean meal, 3% glucose, 0.5% Pharmamedia, 0.1% yeast extract and 0.3% $CaCO_3$. Tank fermentation was carried out at 28° C. with stirring at 250 rpm and aeration at 120 liter/min. The production reached a maximum after 115 hours fermentation.

EXAMPLE 2

Isolation and Purification of 3,7-Dihydroxytropolone (BU-3129T)

The culture broth (208 L, pH 9.06) obtained according to the method of Example 1 was separated into the mycelial cake and the supernate with the aid of a continuous centrifuge (Kokusan H-600). The supernate (pH 9.0) was passed through a column packed with Diaion HP-20 (10L) to adsorb the impurities. The passed supernate was adjusted to pH 4.0 by 6N HCl and applied again on a Diaion HP-20 column (15 L). After washing with 20 L of water, the column was developed with a mixture of acetone-0.1N NH$_4$OH (1:1, v/v, 40 L). The active fractions as determined by paper disc assay against *Cryptococcus neoformans* IAM 4514, were pooled, evaporated in vacuo and lyophilized yielding 370 g of crude solid. A 37 g sample of this crude solid was charged on a column of Sephadex G-25 ($\phi$8.0 ×110 cm, 5L) which was developed with water. Evaporation of the active fractions followed by lyophilization of the residue gave a semi-pure sample of BU-3129T (21 mg). The solid was chromatographed on Sephadex LH-20 ($\phi$3.0 ×62 cm, 100 ml) with methanol elution. The fractions containing the major activity were concentrated to yield a nearly homogeneous sample of BU-3129T (6.0 mg). Crystallization from ethanol deposited pale yellow needles of pure BU-3129T (4.0 mg).

We claim:

1. A process for the production of 3,7-dihydroxytropolone which comprises aerobically cultivating a strain of *Streptomyces tropolofaciens* having the identifying characteristics of ATCC 53548, or a 3,7-dihydroxytropolone-producing mutant thereof, in an aqueous nutrient medium containing assimilable sources of carbon and nitrogen until a substantial amount of 3,7-dihydroxytropolone is produced by said organism in said culture medium.

2. The process according to claim 1 which includes the additional step of isolating 3,7-dihydroxytropolone from the culture medium.

* * * * *